(12) United States Patent
Alshaalan et al.

(10) Patent No.: US 12,333,921 B2
(45) Date of Patent: Jun. 17, 2025

(54) UNMANNED AERIAL SYSTEM FOR AUTONOMOUS GAS LEAKAGE DETECTION, QUANTIFICATION, AND MITIGATION

(71) Applicant: SAUDI ARABIAN OIL COMPANY, Dhahran (SA)

(72) Inventors: Yasser A. Alshaalan, Dammam (SA); Omar A. Dubayan, Dammam (SA); Abdulrahman H. Alswaidan, Dammam (SA); Prem Kumar, Dhahran (SA); Aidhah J. Zahrani, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 111 days.

(21) Appl. No.: 18/331,828

(22) Filed: Jun. 8, 2023

(65) Prior Publication Data
US 2024/0412615 A1 Dec. 12, 2024

(51) Int. Cl.
  *G08B 21/16* (2006.01)
  *G01N 33/00* (2006.01)
(52) U.S. Cl.
  CPC ......... *G08B 21/16* (2013.01); *G01N 33/0075* (2013.01)
(58) Field of Classification Search
  CPC .......................... G08B 21/16; G01N 33/0075
  USPC ....................................................... 340/605
  See application file for complete search history.

(56) References Cited

U.S. PATENT DOCUMENTS

| | | | | |
|---|---|---|---|---|
| 6,822,742 B1 * | 11/2004 | Kalayeh | ............ | G01N 21/3504 356/432 |
| 10,520,387 B2 * | 12/2019 | Wang | ............ | G01M 3/22 |
| 11,412,441 B2 | 8/2022 | Crouthamel et al. | | |
| 2004/0263852 A1 * | 12/2004 | Degtiarev | ............ | G01N 21/39 356/437 |
| 2016/0146696 A1 * | 5/2016 | Steele | ............ | G01M 3/04 702/51 |
| 2017/0234757 A1 * | 8/2017 | Wang | ............ | G08B 13/194 340/539.1 |
| 2018/0222581 A1 * | 8/2018 | Nagasawa | ............ | G01B 11/00 |
| 2018/0292374 A1 * | 10/2018 | Dittberner | ............ | G08G 5/55 |
| 2018/0327091 A1 * | 11/2018 | Burks | ............ | B64U 50/13 |
| 2019/0154536 A1 * | 5/2019 | Wang | ............ | G01M 3/007 |
| 2021/0335117 A1 * | 10/2021 | Duggan | ............ | G01S 19/01 |
| 2022/0357231 A1 * | 11/2022 | Nahata | ............ | G01M 3/22 |

(Continued)

*Primary Examiner* — Zhen Y Wu
(74) *Attorney, Agent, or Firm* — Osha Bergman Watanabe & Burton LLP

(57) ABSTRACT

A method for locating and mitigating a gas leak includes receiving gas leak sensory data from one or more gas leak detection sensors disposed on a gas-handling system and further receiving environmental conditions data. The method further includes dispatching an unmanned aerial vehicle (UAV) to a location upon detecting a gas leak using the one or more gas leak detection sensors and collecting one or more visual images of the gas-handling system using the UAV once it has reached the location. The method further includes determining, using the one or more visual images, the gas leak sensory data, and the environmental conditions data, a gas leak location and identifying components of the gas-handling system impacted by the gas leak given the gas leak location. The method further includes determining a mitigation action and resolving the gas leak by applying the mitigation action.

20 Claims, 7 Drawing Sheets

(56) References Cited

U.S. PATENT DOCUMENTS

2023/0274651 A1* 8/2023 McGuire .............. G05D 1/689
                                                    701/3
2024/0028051 A1* 1/2024 Miller, II ................ G05D 1/46

* cited by examiner

UNMANNED AERIAL SYSTEM FOR AUTONOMOUS GAS LEAKAGE DETECTION, QUANTIFICATION, AND MITIGATION

BACKGROUND

Gas leaks may occur at processing plants, industrial facilities, and transportation systems (e.g., vehicles, pipelines, etc.). Gas leaks pose a number of health and safety hazards, can cause equipment failure, and may have negative economic impacts on associated operations and processes.

Typically, once a gas leak is detected, for example, by a gas leak sensor, a human operator is dispatched to locate the origin of the gas leak. Upon locating the gas leak, affected processes, system, and equipment may be identified and isolated and an evaluation may occur to determine repair and mitigation strategies. Generally, this process of dispatching a human operator, identifying the gas leak location, isolating affected processes and system, and determining a repair and/or equipment replacement plan is a slow process resulting in undesired downtime and economic costs. Further, dispatching a human operator to accurately locate a gas leak presents a health and safety risk to the human operator (e.g., gas inhalation, explosion hazard (if gas or gas and air mixture is combustible)) and introduces opportunity for human-induced errors to occur. Accordingly, there exists a need to quickly and accurately identify the location of a gas leak, once a leak is detected, and recommend tailored mitigation options and/or repair, maintenance, and equipment replacement plans without compromising the health and safety of a human operator.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments disclosed herein generally relate to a method for locating and mitigating a gas leak. The method includes receiving gas leak sensory data from one or more gas leak detection sensors disposed on a gas-handling system and receiving environmental conditions data. The method further includes dispatching an unmanned aerial vehicle (UAV) to a location upon detecting a gas leak using the one or more gas leak detection sensors and collecting one or more visual images of the gas-handling system using the UAV once it has reached the location. The method further includes determining, using the one or more visual images, the gas leak sensory data, and the environmental conditions data, a gas leak location and identifying components of the gas-handling system impacted by the gas leak given the gas leak location. The method further includes determining a mitigation action and resolving the gas leak by applying the mitigation action.

In another aspect, embodiments disclosed herein generally relate to a system that includes one or more gas leak detection sensors disposed throughout a gas-handling system and an autonomous unmanned aerial vehicle (UAV) system configured to dispatch a UAV to a desired location. In general, the UAV may be flown without human interaction and is configured to acquire one or more visual images upon arriving at the desired location. The system further includes a computer communicably connected to the autonomous UAV system with one or more computer processors and a non-transitory computer readable medium storing instructions executable by a computer processor. The instructions include functionality for receiving gas leak sensory data from the one or more gas leak detection sensors, determining the desired location, and transmitting a signal to the autonomous UAV system to dispatch the UAV to the desired location upon detecting a gas leak using the one or more gas leak detection sensors. The instructions further include functionality for receiving environmental conditions data, receiving the one or more visual images, and determining, using the one or more visual images, the gas leak sensory data, and the environmental conditions data, a gas leak location. The instructions further include functionality for identifying components of the gas-handling system impacted by the gas leak given the gas leak location and determining a mitigation action.

In yet another aspect, embodiments disclosed herein generally relate to a non-transitory computer-readable memory that includes computer-executable instructions stored thereon that, when executed on a processor, cause the processor to perform the following steps. The steps include receiving gas leak sensory data from one or more gas leak detection sensors disposed on a gas-handling system, receiving environmental conditions data, and dispatching an unmanned aerial vehicle (UAV) to a location upon detecting a gas leak using the one or more gas leak detection sensors. The steps further include collecting one or more visual images of the gas-handling system using the UAV once it has reached the location and determining, using the one or more visual images, the gas leak sensory data, and the environmental conditions data, a gas leak location. The steps further include identifying components of the gas-handling system impacted by the gas leak given the gas leak location and determining a mitigation action.

Other aspects and advantages of the claimed subject matter will be apparent from the following description and the appended claims.

DETAILED DESCRIPTION

Figure 1:
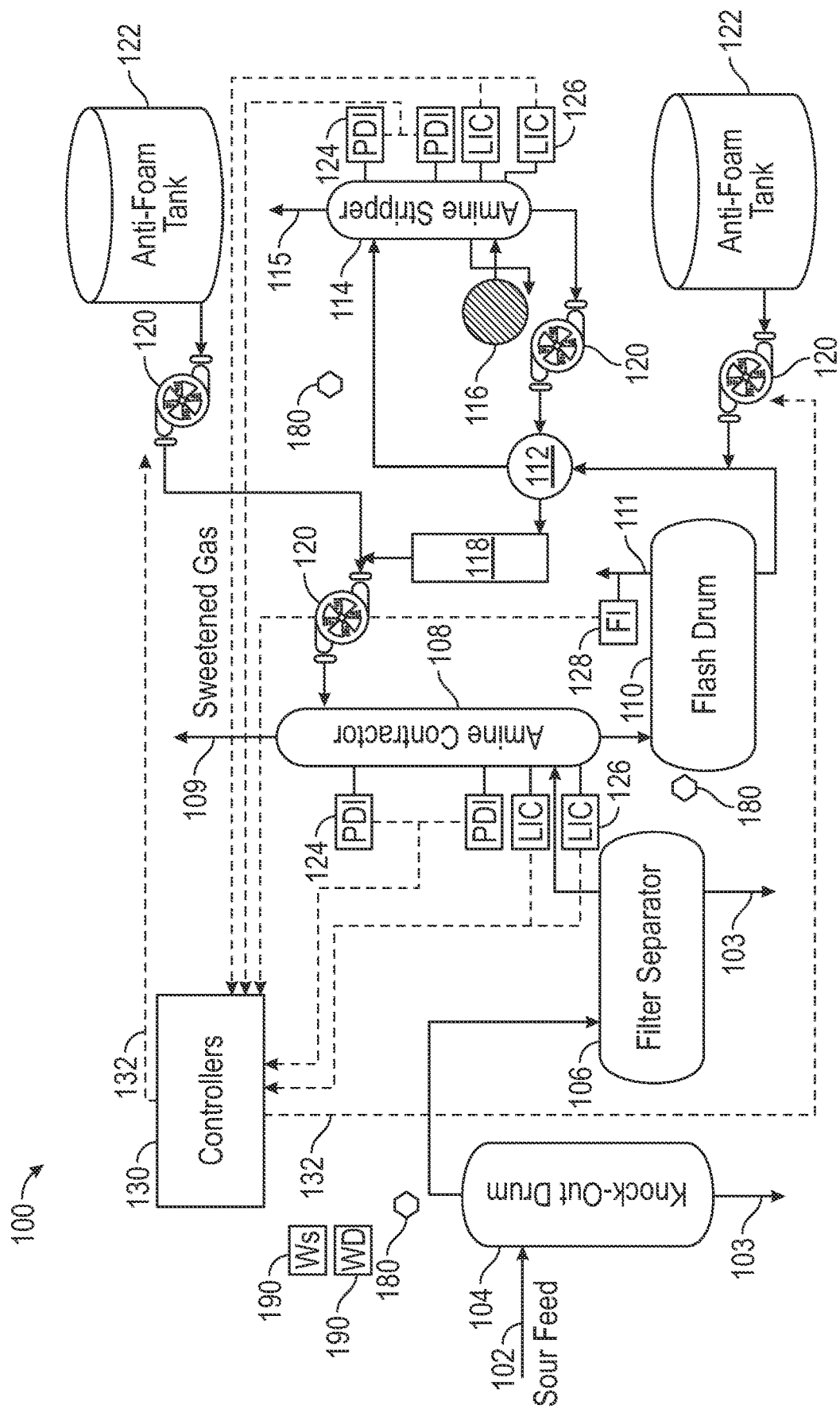
FIG. 1 depicts an example gas processing plant, in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "acoustic signal" includes reference to one or more of such acoustic signals.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

In one aspect, embodiments disclosed herein relate to a gas leak detection and resolution system capable of receiving gas leak sensory data from one or more gas leak sensors disposed throughout or near a gas-handling system, dispatch one or more unmanned aerial vehicles (UAVs) (e.g., drones) to locate the detected gas leak, and recommend tailored options to resolve the gas leak and quickly operationalize any affected systems and/or processes. The gas leak detection and resolution system described herein is process and facility agnostic such that it may generally be employed in any gas-handling system, or process of a gas-handling system. Further, the gas leak detection and resolution system can predict the spread of a gas cloud and identify high-risk spatial areas, for example, areas where a combustible gas (or gas-air mixture) may accumulate near an ignition source (e.g., a hot object, an open flame, etc.). Further, using UAV data collected from the one or more UAVs, the gas leak detection and resolution system may generate an incident model that graphically visualizes the gas leak and its surroundings including the spread of the gas leak cloud and affected systems.

Processes of the gas leak detection and resolution system can operate continuously and in real time, where real time is colloquially understood to indicate that data and signals are received, transmitted, and processed within a short period (e.g., within seconds) after a triggering event (e.g., measurement from a sensor). Thus, the gas leak detection and resolution system can quickly and efficiently react to, evaluate, and mitigate a detected gas leak regardless of the time (e.g., overnight when personnel numbers may be reduced) and, in some embodiments, without human interaction.

As stated, the gas leak detection and resolution system may be used with any gas-handling system including, but not limited to gas processing plants; industrial facilities; gas-handling vehicles; and pipelines. Herein, a gas processing plant will be used as an example to depict aspects of the gas leak detection and resolution system and its usage, in accordance with one or more embodiments. However, one with ordinary skill in the art will recognize that use of the gas leak detection and resolution system described herein is not limited to gas processing plants such that depictions of an example gas processing plant do not impose a limitation on the instant disclosure.

FIG. 1 depicts the flow of a fluid through an example gas processing plant (100). One with ordinary skill in the art will recognize that gas processing plants (100) may be configured in a variety of ways according to plant-specific needs and applications. As such, the equipment and associated processes shown in FIG. 1, and their arrangement, are non-limiting. Further, a given process of a gas processing plant is often associated with a mechanical device, such as a tank or a heat exchanger. For the purposes of FIG. 1, components of the gas processing plant (100) may be described according to their process or their mechanical form without undue ambiguity. In other words, a tank or a drum may herein be described as a process or a mechanical device.

In the context of the field of oil and gas, in general, a production fluid that may contain oil, gas, water (or brine), and solid particulates is separated into its constituents and further refined. The gas processing plant (100) depicted in FIG. 1, receives a contaminated fluid, where "contamination" simply indicates the fluid is not in its desired state, processes the fluid, and produces a refined gas. Depending on the intention and design of a gas processing plant, contaminants may include solid particulates (e.g., sand), liquid hydrocarbons (e.g., oil), and water (e.g., formation brine).

As shown in FIG. 1, an incoming contaminated fluid (102) is sent to a gas processing plant (100) via a pipeline. The incoming contaminated fluid (102) may be called the "sour feed." The incoming contaminated fluid (102) may be multiphase and be composed of a variety of solid, liquid, and gaseous constituents. For example, the incoming contaminated fluid (102) may contain solid particulates like sand, mineral precipitates such as pipe scale, and corroded pipe, liquid such as water, and gases like carbon dioxide ($CO_2$) and hydrogen sulfide ($H_2S$). In particular, $H_2S$, in the presence of water, is highly corrosive and should be removed to prevent a leak in the pipeline. Additionally, the incoming contaminated fluid (102) may contain liquid and gas forms of various hydrocarbons.

In the example gas processing plant (100) of FIG. 1, the incoming contaminated fluid (102), or sour feed, is processed by a knock-out drum (104). The knock-out drum (104) performs bulk separation of gas and liquid. Liquid, separated from the incoming contaminated fluid (102), exits the knock-out drum (104) through a liquid exit (103).

From the knock-out drum (104), the bulk gas is processed by a filter separator (106). A filter separator (106) removes impurities such as mineral precipitates (e.g. pipe scale), water, liquid hydrocarbons, and iron sulfide from the fluid. A filter separator (106) uses filter elements, such as a replaceable sock or a coalescing filter, rather than mechanical components to separate out contaminants. Typically, a filter separator (106) may be composed of 1 or 2 stages and may operate at high or low pressure. Again, the unwanted portions of the incoming contaminated fluid (102) exit the filter separator (106) through an exit (103).

After the filter separator (106), the incoming contaminated fluid (102) has been reduced to a gaseous stream. The gaseous stream undergoes another purifying process through an amine contactor (108). An amine contactor (108) absorbs carbon dioxide ($CO_2$) and/or hydrogen sulfide ($H_2S$) contaminants from the gaseous stream. In general, an amine contactor (108) receives the partially processed incoming contaminated fluid (102), or gaseous stream, and a "lean"

amine liquid. Common amines are diethanolamine (DEA), monoethanolamine (MEA), methyldiethanolamine (MDEA), diisopropanolamine (DIPA), and aminoethoxyethanol (Diglycolamine) (DGA). The contact between the gaseous stream and the lean amine liquid drives the absorption of CO2 and/or H2S into the amine liquid from the gaseous stream. As a result, decontaminated gas (109), also known as "sweetened gas", may exit the amine contactor (108). The decontaminated gas (109) should be checked to make sure it meets specifications. If the decontaminated gas (109) does not meet specifications, this is indicative that control parameters within the gas processing plant (100) require adjustment. The processes of the knock-out drum (104), filter separator (106), and amine contactor (108) effectively transform the incoming contaminated fluid (102) to a decontaminated gas (109) and complete the objective of the example gas processing plant (100) shown in FIG. 1. However, in general, additional processes are required to maintain a gas processing plant (100) in an operational state. For example, the liquid amine that has absorbed the unwanted CO2 and H2S, which is called "rich" amine, is sent to an amine stripper for removal of its contaminants and re-conditioning.

As shown in FIG. 1, the contaminated amine is first sent to a flash drum (110). This process consists of throttling the contaminated amines causing a pressure drop such that vapors are formed. The vapors exit the flash drum where they undergo further processing, such as being passed to an oxidizer. These steps have been omitted from FIG. 1 for brevity.

The remaining liquid contaminated amines enter a heat exchanger (112). The heat exchanger (112) recovers heat from the decontaminated amine leaving the amine stripper (114), which is described below. Consequently, the heat exchanger (112) heats the contaminated amine before entering the amine stripper (114).

The amine stripper (114) serves to remove the absorbed contaminants, such as H2S and CO2, from the amine solution so that it can be used again in the amine contactor (108). The amine stripper (114) is equipped with a reboiler (116). The amine stripper (114) contains a tray column consisting of a stripping section and a water wash section at the top. The reboiler (116) takes the amine solution located at the bottom of the amine stripper (114) and partially boils it. Steam (hot, gaseous water) is typically used as the heat source in the reboiler (116). Steam, typically sourced from the reboiler (116), flows up the column in the amine stripper (114) and contacts the contaminated amine solution flowing down within the column. As the contaminated amine contacts the steam, it is heated up and the contaminants are stripped out of the rich amine solution and flow to the stripping section of the column.

The stripped gases, commonly referred to as amine acid gas, leaves the amine stripper through a stripped gas exit (115). The stripped gases undergo further processing, such as condensing out the water and passing the remaining acid gases to a sulfur recovery process, but these processes are not shown in FIG. 1 for brevity.

The decontaminated amine solution, leaving the bottom of the amine stripper (114), contains very low quantities of acid gas (such as H2S). This decontaminated amine solution may be recycled in a lean amine storage tank (not shown) and/or returned to the amine contactor (108). As shown in FIG. 1, the decontaminated amine solution leaving the amine stripper (114) is passed through the heat exchanger (112), to transfer heat to the contaminated amine solution leaving the flash drum (110). After passing through the heat exchanger (112), the decontaminated amine solution may be further cooled in a cooler (118) before being returned to the amine contactor (108).

The transport of the various fluids of the gas processing plant of FIG. 1 is facilitated by a plurality of pumps and/or compressors (120) disposed throughout the system. The type of pump or compressor (120), and the location may be altered and arranged according to plant-specific needs.

As noted above, it is emphasized that a gas processing facility (100) may implement different processes and mechanisms for achieving adequate gas processing. Some processes may include compression, stabilization, and dehydration. The gas processing plant (100) may also encompass the treatment of removed water for disposal through processes such as filtration and deionization. Additionally, elements for heating and cooling may be provided to prevent the formation of hydrates, and mitigate corrosion and aid in dehydration, respectively. With respect to decontaminating the incoming contaminated fluid (102), other chemical and physical washes may be used without departing from the scope of this disclosure.

As shown in FIG. 1, the processes may be monitored and controlled by a plurality of sensors and controllers. As an example, the amine contactor (108) and amine stripper (114) are both equipped with pressure differential indicators (PDI) (124) and level indicators (LIC) (126) in FIG. 1. Additionally, FIG. 1 depicts a flow indicator (FI) (128) connected to the exit of the flashed gases exiting the flash drum (110). The PDIs, LICs, and FIs, which are sensors, may send information regarding the pressure difference measured across processes, the quantity and level of fluids present, and the flow rate of fluids, respectively, to one or more controllers (130). Flow indicators (FIs) disposed throughout the gas processing plant (100) may be multiphase flow indicators. In some embodiments, one or more gas leak sensors (180), selected to detect one or more expected gas compositions to be present in the gas processing plant (100), may also be provided at one or more locations in the gas processing plant (100) (e.g., on one or more pipes or equipment units). In one or more embodiments, one or more environmental sensors (190) are provided at one or more locations in the gas processing plant (100) (e.g., a wind speed (WS) sensor and a wind direction (WD) sensor). More information regarding environmental sensors is provided later in the instant disclosure.

The one or more controllers (130) may herein be referred to as "controllers" or "controller" where appropriate. Controllers (130) may be distributed, local to the processes and associated device, global, connected, etc. Controllers (130) may include or consist of a programmable logic controller (PLC), a distributed control system (DCS), a supervisory control and data acquisition (SCADA), and/or a remote terminal unit (RTU). For example, a programmable logic controller (PLC) may control valve states, fluid levels, pipe pressures, warning alarms, and/or pressure releases throughout a gas processing plant (100). In particular, a programmable logic controller (PLC) may be a ruggedized computer system with functionality to withstand vibrations, extreme temperatures, wet conditions, and/or dusty conditions, for example, around a refinery. A distributed control system may be a computer system for managing various processes at a gas processing plant (100) using multiple control loops. As such, a distributed control system may include various autonomous controllers (130) (such as remote terminal units) positioned at different locations throughout the facility to manage operations and monitor processes. Likewise, a distributed control system may include no single centralized computer for managing control loops and other operations. On the other hand, a SCADA system may include a control system that includes functionality for enabling monitoring and issuing of process commands through local control at a gas processing facility (100) as well as remote control outside the facility. With respect to an RTU, an RTU may include hardware and/or software, such as a microprocessor, that connects sensors and/or actuators using network connections to perform various processes in the automation system. Likewise, a control system may be coupled to one or more gas processing plant (100) devices.

FIG. 1 also depicts anti-foam tanks (122) which contain an anti-foaming agent that may be injected, by use of a pump (120) and a controller (130), into different parts of the gas processing system as indicated by the dashed line (132). The anti-foam tanks (122) and injection of an anti-foaming agent into the sub-processes of the gas processing plant (100) may be necessary because a frequent problem in gas processing plants (100) is foaming.

Figure 2:
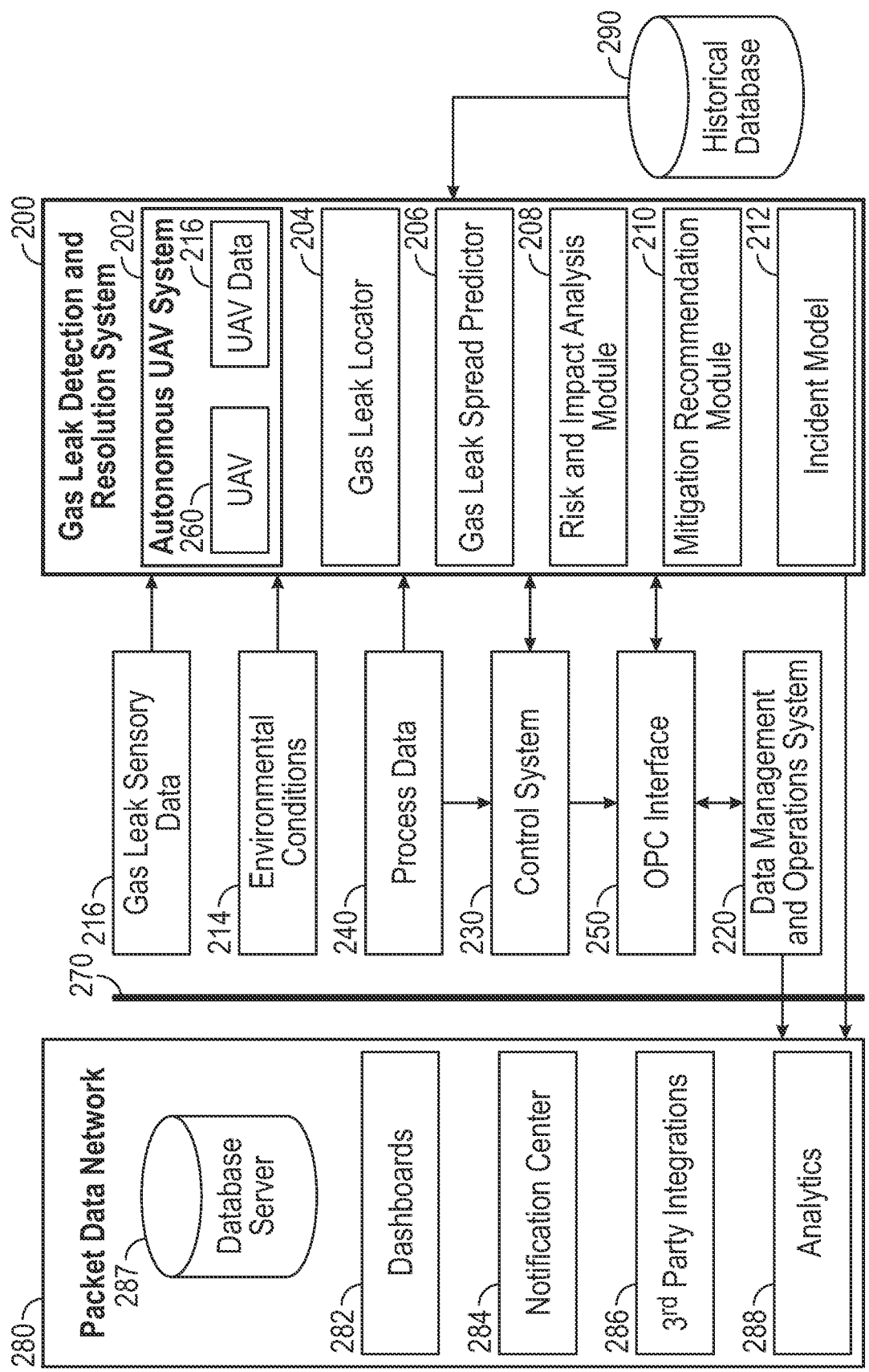
FIG. 2 depicts a system in accordance with one or more embodiments.

FIG. 2 depicts the gas leak detection and resolution system (200) in accordance with one or more embodiments. In FIG. 2, the gas leak detection and resolution system (200) is depicted as being composed of various components and/or modules, where the components and/or modules may interact with each other. One with ordinary skill in the art will recognize that the partitioning, organization, and interaction of the components and/or modules of the gas leak detection and resolution system (200) in FIG. 2 is intended to promote clear discussion and should not be considered fixed or limiting. For example, FIG. 2 depicts a gas leak spread predictor (206), a risk and impact analysis module (208), and a mitigation recommendation module (210) as separate and independent entities, however, in one or more embodiments, the functionality provided by these components and/or modules may be performed by a single system or module.

In one or more embodiments, the gas leak detection and resolution system (200) is configured to receive gas leak sensory data (216). Gas leak sensory data (216) may include signals and data packets from one or more gas leak sensors disposed throughout or near a gas-handling system (e.g., gas processing plant (100)). Each of the one or more gas leak sensors can detect, in one form or another, the presence of a gas. Example gas leak sensors may include hydrogen sulfide (H2S) sensors and lower explosive limit (LEL) sensors. Sometimes, in the literature, gas leak sensors are discussed in terms of lower-level components, such as sensing device (e.g., electromechanical cell), controller (or microcontroller), and transmitter. Herein, gas leak sensors are described as devices capable of measuring, sensing, and/or detecting the presence of one or more gaseous molecules and include all the components required to fully functionalize the sensor and to transmit a signal that indicates the presence, detection, and/or amount of the one or more gaseous molecules. That is, herein, a gas leak sensor may include a sensing device, a controller, and a transmitter.

Generally, an H2S Sensor detects low level hydrogen sulfide at ppm (parts per million) levels. Typically, an H2S sensor outputs a current output proportional to the ppm level of H2S that diffuses into the sensor through a hydrophobic membrane. Thus, a current level may be calibrated to an amount of H2S present near the H2S sensor and the amount H2S may be transmitted to the gas leak detection and resolution system (200) as gas leak sensory data (216).

Often, combustible gases and solvents may be characterized with a lower explosive limit (LEL). LEL is defined as the lowest concentration (by percentage) of a gas or vapor in air (or in its expected environment) that is capable of combusting in the presence of an ignition source or upon receiving an initiation stimulus (e.g., open flame, high temperature object, electrical current or arc, etc.). Concentrations lower than an LEL level of 100% are said to be "too lean" to burn (i.e., a relatively low fuel to air ratio). Thus, an LEL sensor may specify the amount of gas present near the detector a percentage (%) of LEL.

In accordance with one or more embodiments, the gas leak detection and resolution system (200) is configured to receive environmental conditions data (214). Environmental conditions data (214) may include signal and/or data packets from one or more environmental sensors disposed throughout or near a gas-handling system (e.g., gas processing plant (100)). Environmental sensors may include, but are not limited to: temperature sensor, humidity sensor, barometric pressure sensor, wind speed sensor, and wind direction sensor. Herein, like unto the gas leak sensors, environmental sensors are described as devices capable of measuring, sensing, and/or detecting an environmental quantity (e.g., humidity) and include all the components required to fully functionalize the sensor and to transmit a signal representative of the measured quantity. That is, herein, an environmental sensor may include a sensing device, a controller, and a transmitter.

The position of each gas leak sensor is known by the gas leak detection and resolution system (200) and is represented by a set of coordinates. In general, N gas leak sensors may be disposed near or throughout a gas-handling area (e.g., gas processing plant (100)). A coordinate system (e.g., a cartesian coordinate system) may be established with respect to a gas-handling system. As such, the location of each of the N gas leak sensors may be represented by one or more coordinates with respect to the established coordinate system. In one or more embodiments, the position of a gas leak sensor is given by an x-coordinate and a y-coordinate, written succinctly as (x, y), where the values of x and y indicate a distance along an x-axis and a y-axis defined by the established coordinate system, respectively. Note, that while often convenient, the x-axis and y-axis need not be orthogonal. In one or more embodiments, the position of a gas leak sensor is further defined by a third coordinate, for example, a z-coordinate representing a distance along z-axis defined by the established coordinate system. Typically, the z-coordinate represents the distance of the gas leak sensor above a ground level (or floor). Without loss of generality, the positions of each of the N gas leak sensors disposed near or throughout a gas-handling system may be stored and/or represented as a gas leak sensor position vector. For example, considering the case where the position of a gas leak sensor is given by an x-coordinate and a y-coordinate, the gas leak sensor position vector may be represented as $[(x_1, y_1), (x_2, y_2), \ldots, (x_n, y_n), \ldots, (x_{N-1}, Y_{N-1}), (x_N, Y_N)]$, where n indicates the $n^{th}$ gas leak sensor of N gas leak sensors. In general, N is greater than or equal to one (i.e., $N \geq 1$). In accordance with one or more embodiments, the gas leak sensor position vector is stored in, or accessible by, the gas leak detection and resolution system (200) such that the position or location of any gas leak sensor disposed near or throughout a gas-handling system is known to the gas leak detection and resolution system (200).

In one or more embodiments, one or more environmental sensors are clustered, or otherwise grouped together, as an environment sensing stations (e.g., a weather station). One or more environment sensing stations may be disposed near a gas-handling system. In other embodiments, environmental sensors are disposed on an unmanned aerial vehicle (UAV). UAVs will be discussed in greater detail below, however, for now it is stated that, in one more embodiments, environmental conditions data (214) is received from a UAV (260), where the measurements contained in the environmental conditions data (214) are local to the UAV (260) and the UAV (260) may be dispatched near a gas-handling system (e.g., gas processing plant (100)). In one or more embodiments, environmental conditions data (214) is received from a third-party system (e.g., government-owned weather station) through an application programmer interface (API). That is, in one or more embodiments, environmental conditions data (214) is generated through a query to an external environment sensor system, where the queried environmental conditions data (214) is expected to coincide with an area encompassing or proximate to a gas-handling system.

In accordance with one or more embodiments, the gas leak detection and resolution system (200) is configured to receive process data (240). Process data includes any control parameters or sensor data associated with a gas-handling system that are not already included in the gas leak sensory data (216) and the environmental conditions data (214). For example, considering the example gas processing plant (100) of FIG. 1, process data (240) may include measurements acquired by pressure differential indicators (PDI) (124), level indicators (LIC) (126), and flow indicators (FI) (128). Process data (240) may further include pump (120) settings and any data generally received, transmitted, or controlled by controllers (130) (e.g., a distributed control system (DCS)).

In accordance with one or more embodiments, the gas leak detection and resolution system (200) includes an autonomous unmanned aerial vehicle (UAV) system (202). The autonomous UAV system (202) includes one or more UAVs (260) that may be dispatched upon detection of a gas leak. The present disclosure places no restrictions on the type of UAV (260) employed by the autonomous UAV system (202). In general, the UAV (260) may be a fix-wing type or a rotary-wing type (e.g., quadcopter, tricopter, etc.). In one or more embodiments, the UAV (260) is referred to as a "drone."

In one or more embodiments, a UAV (260) may be dispatched by the gas leak detection and resolution system (200) to the vicinity of one or more gas leak sensors that are actively detecting, or recently detected, as gas leak. In one or more embodiments, each UAV (260) may operate autonomously without the need for human guidance and/or control. In general, each UAV (260) of the autonomous UAV system (202) possesses one or more cameras and an object detection and avoidance system. In some embodiments, the UAV (260) further includes additional sensors, such as ultrasonic sensors and light detection and ranging (LiDAR) sensors to detect the presence and proximity of objects surrounding the UAV (260). A UAV (260) may further include global positioning system (GPS) components for positioning, navigation, and timing (PNT) services. The object detection and avoidance system is configured to receive sensory inputs from the UAV (260), for example, visual data acquired from the one or more cameras, object proximity data, and GPS data. The object detection and avoidance system may fuse sensory inputs to maneuver the UAV (260) to a desired location (e.g., above a given gas leak sensor) without colliding with an object (e.g., a flue-gas stack).

In one or more embodiments, a UAV (260) of the autonomous UAV system (202) possesses thermal imaging capabilities. Thermal imaging may be performed using a thermal camera, for example, a camera outfitted with an infrared sensor sensitive to infrared light. That is, in one or more embodiments, a UAV (260) includes both a visual camera and a thermal camera. In some embodiments, both visual imaging and thermal imaging are performed using the same camera using one or more photosensors and/or light filters (i.e., a filter that limits incoming light according to frequency (or wavelength)). Thermal images acquired by the UAV (260) may be used to identify and locate high temperature objects, or other potential ignition sources, near a gas leak.

In accordance with one or more embodiments, a UAV (260) of the autonomous UAV system (202) can simultaneously self-locate and map its surrounding environment, a process known as simultaneous localization and mapping (SLAM). Generally, SLAM is a method used principally by autonomous vehicles to map (spatially orient surrounding objects) and localize the vehicle in that map at the same time. In one or more embodiments, a SLAM algorithm may facilitate or be a part of the object detection and avoidance system of the UAV (260). Further, a SLAM algorithm may be used to plan a path for the UAV (260) to travel in order to safely arrive at desired destination (e.g., near or above an active gas leak sensor). The SLAM algorithm can run in real time or traceable time. Methods used by the SLAM algorithm may include, but are not limited to: particle filter; extended Kalman filter; and covariance intersection.

Each of the one or more UAVs (260) can communicate with the gas leak detection and resolution system (200) and thus components of the gas leak detection and resolution system (200), through wireless or wired connections or a combination of wireless and wired connections. Wireless communication may be facilitated through RFID, NFC, low-energy Bluetooth, low-energy wireless, low-energy radio protocols, LTE-A, and WiFi-Direct technologies. In one or more embodiments, a UAV (260) communicates with gas leak detection and resolution system (200), or its components and/or modules, using a wireless protocol. In other embodiments, a UAV (260) establishes a wireless link with a ground control system and the ground control system has a wired connection (e.g., ethernet, USB, etc.) with the gas leak detection and resolution system (200). In general, one or more ground control stations may be disposed throughout, or near, a gas-handling area. In one or more embodiments, ground control systems further act as docking and charging stations for one or more UAVs (260) when not in use. Communication between a UAV (260) and the gas leak detection and resolution system (200) includes any transferred data and control signals that may be sent bidirectionally between UAV (260) and the gas leak detection and resolution system (200). For example, a UAV (260) may transfer, through an established communication link, its location and acquired visual images to the gas leak detection and resolution system (200). Likewise, the gas leak detection and resolution system (200) may send a control signal to the UAV (260) specifying a target destination for the UAV (160). Other data that may be communicated between a UAV (160) and the gas leak detection and resolution system (200) include the battery level of the UAV (160) and operational parameters of the UAV (160) (e.g., internal temperature, rotary speeds, etc.). Herein, data sent, transferred, or communicated to the gas leak detection and resolution system (200) from the one or more UAVs (160) is referred to a UAV data (216).

In accordance with one or more embodiments, the gas leak detection and resolution system (200) performs photogrammetric analysis using received UAV data (216). Photogrammetry, defined generally, is the process of collecting and/or displaying physical information from two-dimensional (2D) photos or images. Thus, in one or more embodiments, the gas leak detection and resolution system (200) processes one or more images acquired by a UAV (260) (and received as UAV data (216)) to form an incident model (212). In accordance with one or more embodiments, UAV data (216) (and gas leak sensory data (216) and environmental conditions data (214)) may undergo preprocessing. For example, preprocessing of acquired visual images may include normalizing the images. Additional techniques such as aggregating multiple images, or other methods designed to reduce noise in an image and increase image quality may be employed. One with ordinary skill in the art will appreciate that many image preprocessing techniques exist and the fact that they are not enumerated herein does not impose a limit on the present disclosure. In some embodiments, preprocessing may not be required.

In accordance with one or more embodiments, the incident model (212) includes a 2D or 3D representation of the region or area represented in the received image(s). In one or more embodiments, the incident model (212) includes a 2D diagram of the region or area represented in the received image(s), such as the depiction of a gas processing plant (100) in FIG. 1. In other embodiments, the gas leak detection and resolution system (200) generates a piping and instrumentation diagram (P&ID) of the represented area or region for use in the incident model (212). The incident model (212) may further visualize the location of a gas leak and the spread, or boundary, of a leaked gas relative to objects in a gas-handling area, as will be explained in greater detail below.

In one or more embodiments, the computational requirement or burden of a UAV (260) is reduced by performing calculations using one or more computers included in the gas leak detection and resolution system (200) (computers such as that depicted in FIG. 7) or by one or more ground control systems. For example, in one or more embodiments, a UAV (260) transmits its position and acquired visual image(s) to the gas leak detection and resolution system (200) and an object detection routine or method is performed using one of the one or more computers of the gas leak detection and resolution system (200). Upon detection of object(s), a UAV path or flight plan may be transmitted from the gas leak detection and resolution system (200) to the UAV (260). In one or more embodiments, object detection from acquired visual image(s) is performed using one or more machine-learned models (e.g., a convolutional neural network) and/or computer vision techniques. General concepts of machine-learning will be described in greater detail later in the instant disclosure. For now, however, it is noted that in one or more embodiments the gas leak detection and resolution system (200) is connected to a historical database (290). The historical database may include acquired visual and thermal images, gas leak sensory data, environmental conditions data, etc. of one or more other gas-handling systems as well as accompanying labels or annotations such as the location of a gas leak, labelled objects, identification of high-risk areas, etc. As such, in instances where a machine-learned model is employed by the gas leak detection and resolution system (200), the machine-learned model may be "trained" using the historical database. Again, a basic introduction to training a machine-learned model is presented later in the instant disclosure.

In accordance with one or more embodiments, the gas leak detection and resolution system (200) further includes a gas leak locator (204). Gas leak sensors that have detected a gas leak may not be located at the site of a gas leak. In general, the gas leak locator (204) considers the positions of all gas leak sensors that have detected a gas leak (as indicated through the gas leak sensory data (216)) and, in some embodiments, received UAV data (216) and environmental conditions data (214) to pinpoint the location of the gas leak. In one or more embodiments, the gas leak locator (204) uses a triangulation method to determine the location of the gas leak given gas leak sensory data (216), while also considering time differences between activate gas leak sensors when two or more gas leak sensors detect a leak, in view of environmental conditions data (214) such as wind speed and wind direction. In one or more embodiments, the gas leak locator (204) predicts the location of a gas leak using a machine-learned model given the gas leak sensory data (216), environmental conditions data (214), and UAV data (216). In some embodiments, the gas leak locator (204) may transmit signals to a UAV (260) to direct the UAV (260) to explore additional regions or areas to better pinpoint the location of a gas leak.

In accordance with one or more embodiments, the gas leak detection and resolution system (200) further includes a gas leak spread predictor (206). The gas leak spread predictor (206) models the spread of a leaked gas, or the boundary of area or volume where a leaked gas is present. The gas leak spread predictor (206) may use an analytical model composed of one or more equations or a computational model. Generally, a computational model discretizes a region into cells or grid points and applies a set of equations that govern the behavior of fluid, where the fluid may have more than one constituents (e.g., air and a leaked gas), to each cell or grid point in a self-consistent manner (i.e., respecting global and local physical constraints such as the conservation of mass). In one or more embodiments, equations used in either the analytical model or the computational model are parameterized by one or more environmental parameters measured by one or more environmental sensors and received by the gas leak detection and resolution system (200) as environmental conditions data (214). For example, an equation that describes the diffusion of the leaked gas into the surrounding environment (e.g., air) may be parameterized by barometric pressure, temperature, and humidity. As another example, one or more equations purposed to model convection of a fluid may be parameterized by wind speed and wind direction. The gas leak spread predictor (206) may update a predicted boundary of gas spread as new data is received (e.g., position of newly activated gas leak sensor, changes in environmental conditions, etc.). In one or more embodiments, the gas leak spread predictor (206) may further model, or otherwise account for, the equipment and physical structures of the gas-handling system. Thus, the gas leak spread predictor (206) may identify obstructions to the flow of a leaked gas (and the surrounding fluid, e.g., air), areas of flow-eddies, high fluid current areas, and so-called "dead zones" where fluid movement is stagnant.

In one or more embodiments, the gas leak spread predictor (206) uses a computational fluid dynamics (CFD) model to model the spread of a gas leak through time. In general, the CFD model discretizes a region into cells and models the diffusion and convection of gas (which may be multi-constituent) between cells through time. The CFD may implement a discrete version of the Navier-Stokes equations which may be informed, or parameterized, by environmental conditions data (214). For example, in one or more embodiments, the diffusion rate of gas may be dependent on the ambient temperature and humidity and convection may largely be driven by wind speed and direction data.

Generally, the gas leak spread predictor (206) can predict the area or volume containing a leaked gas, which may be represented as a boundary that encloses the area or volume that contains the leaked gas, at various points in time. The gas leak spread predictor (206) can operate forward in time to predict the boundary of a leaked gas, or a so-called "gas cloud," at a future time. However, there is no restriction that the gas leak spread predictor (206) can only operate forward in time. In general, the gas leak spread predictor (206) may operate backward in time to approximate or determine where a boundary of a leaked gas was at a previous instance in time. Thus, in one or more embodiments, the gas leak spread predictor (206) is used in conjunction with—or used by—the gas leak locator (204) to determine an origin of the gas cloud and therefore the location of the gas leak.

In accordance with one or more embodiments, the gas leak detection and resolution system (200) further includes a risk and impact analysis module (208). In one or more embodiments, the functions of the risk and impact analysis module (208) may be considered two-pronged, where the prongs may interact with one another. A first prong may be directed toward identifying equipment and/or processes of a gas-handling system that may be at risk due to the detection and location of a gas leak. For example, due to a detected and located gas leak, the risk and impact analysis module (208) may determine that an equipment item will receive reduced gas flow and if allowed to continue to operate will result in the degradation or destruction of the equipment item. Further, the first prong of the risk and impact analysis module (208) may determine the impact and overall effect that a detected and located gas leak will have on the associated gas-handling system. For example, the risk and impact analysis module (208) may determine and quantify a reduction in production of the gas-handling system (e.g., gas processing plant) due to equipment and/or processes that must be shut down (as determined by the risk and impact analysis module (208)) and further estimate the economic impact of the gas leak.

In one or more embodiments, a second prong of the risk and impact analysis module (208) is directed toward identifying health and safety risks. In particular, in one or more embodiments, the risk and impact analysis module (208) identifies areas or volumes where accumulation of leaked gas leads to an explosive hazard or increased likelihood of explosion. In identifying areas or volumes with a risk of explosion, the risk and impact analysis module (208) may work in conjunction with—or be combined with—the gas leak spread predictor (206). The risk and impact analysis module (208) may further be equipped to analyze visual and thermal images received from a UAV (260) as UAV data (216). Specifically, thermal image analysis is used to detect potential ignition sources (e.g., open flames, equipment operating at a high temperature, electrical sources, etc.). Thus, the risk of an explosion occurring in an area or volume can further be quantified by factoring in both the presence and concentration of a leaked gas and proximate ignition sources. In one or more embodiments, the physical structures of the gas-handling system, the spread of a leaked gas, and/or identified ignition sources may be visualized with the incident model (212).

In accordance with one or more embodiments, the gas leak detection and resolution system (200) further includes a mitigation recommendation module (210). The mitigation and recommendation module (210), upon detecting and locating a gas leak, identifying affected equipment and/or processes, risk factors (e.g., health and safety risks), and the economic impact caused by the gas leak, provides one or more resolutions (i.e., solutions) and/or mitigation recommendations. A mitigation recommendation may indicate those equipment items and processes that may be temporarily altered (in terms of their operational state or operational parameters) to optimally continue service by a gas-handling system given a gas leak and its associated risks and impact. The mitigation recommendation module (210) may further recommend a repair or equipment replacement strategy in order to resolve (i.e., fix) a detected and located gas leak.

Figure 7:
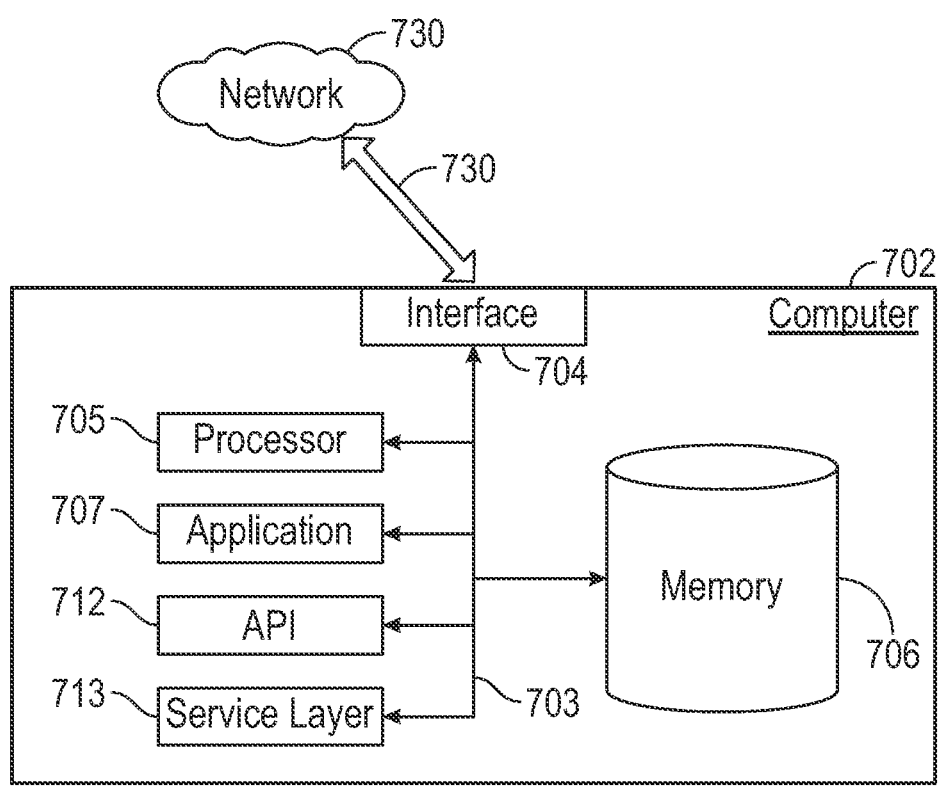
FIG. 7 depicts a system in accordance with one or more embodiments.

Returning to the concept of the incident model (212), generally, the incident model (212) provides a visualization of the gas leak (e.g., the determined gas leak location and the spread of the gas cloud) and the affected processes and/or equipment of the gas-handling system (e.g., gas processing plant (100)) associated with—or near to—the gas leak. The incident model (212) may integrate features of the UAV data (216), gas leak locator (204), gas leak spread predictor (206), risk and impact analysis module (208), and the mitigation recommendation module (210). For example, in one or more embodiments, the incident model (212) provides a rendering (which may be 2D or 3D) of the gas-handling system (e.g., constructed with photogrammetry from UAV data (216)), the exact location of the gas leak (using the gas leak locator (204)), the spread of the gas leak at various instances in time (using the gas leak spread predictor (206)). The incident model (212) may further visually highlight affected equipment and/or processes as well as graphically depict proposed alterations in the gas-handling system according to one or more mitigation recommendations. The incident model (212) may visually present one or more of the above listed aspects of the gas-handling system on a computer system, such as shown in FIG. 7.

In accordance with one or more embodiments, the gas-handling system is monitored and controlled by a control system (230). Examples of a control system (230) may include a distributed control system (DCS) and a supervisory control and data acquisition (SCADA) system. In one or more embodiments, the control system (230) is the same as—or analogous with—the controllers (130) depicted in FIG. 1. In general, the gas leak detection and resolution system (200) can interact and exchange data with the control system (230). For example, in or more embodiments, the gas leak detection and resolution system (200) may instruct (e.g., via a command signal) the control system (230) to shut down or stop one or more processes and/or pieces of equipment that may be negatively impacted by a detected and located gas leak or that may pose a risk to the overall system and/or personnel if permitted to operate in the presence of the detected and located gas leak.

In accordance with one or more embodiments, the gas leak detection and resolution system (200) may further be configured to interact with, be integrated with, or function under a data management and operations system (220). Generally, a data management and operations system (220) is a software suite with functionality for collecting, enriching, storing, and accessing reliable, real-time operations data. An example of a data management and operations system (220) is the AVEVA PI System; available as a vendor-neutral system in the field of oil and gas. In one or more embodiments the data management and operations system (220) provides self-service data visualizations, trending, and analytics related to the gas-handling system. In one or more embodiments, the incident model (212) is visualized through the data management and operations system (220). Still, in accordance with one or more embodiments, the gas leak detection and resolution system (200) is integrated with the data management and operations system (220) such that the data management and operations system (220) is expanded to include the functionality of the gas leak detection and resolution system (200).

In one or more embodiments, data transferred and exchanged between the gas leak detection and resolution system (200) and other systems (e.g., data management and operations system (220)) may pass through, or otherwise be processed with, an open platform communications (OPC) interface (250). OPC is an interoperability standard for secure and reliable data exchange between systems related to industrial automation (and other industries). The OPC standard may be considered as a set of specifications developed by industry vendors, end-users, and software developers, where the specifications define client-server and server-server interfaces providing real-time data transfer, monitoring of alarms and events, and access to historical data and other applications. In one or more embodiments, the OPC interface (250) abstracts specific protocols (such as Modbus, Profibus, etc.) into a standardized interface allowing SCADA systems (and other systems) to interface with a "middle man" that converts generic OPC read/write requests into device-specific requests and vice-versa. In one or more embodiments, the OPC interface (250) provides a safe, fast, and reliable data exchange mechanism between the control system (230) (e.g., DCS, SCADA, etc.) of a gas-handling system (e.g., gas processing plant (100)) and the data management and operations system (220). In one or more embodiments, data transferred between the gas leak detection and resolution system (200) and other systems (e.g., data management and operations system (220)) is formatted such that an OPC interface (250) is not needed.

In accordance with one or more embodiments, the gas leak detection and resolution system (200) can transfer data to an external network (e.g., packet data network (PDN) (280)). In some embodiments, the gas leak detection and resolution system (200) transfers data to an external network through the data management and operations system (220) (which may include an OPC interface (250)). Both modes of data transfer from the gas leak detection and resolution system (200) to an external network (e.g., PDN (280)) are depicted in FIG. 2, and in some embodiments, both modes of data transfer are provided. Examples of the external network may include an information technology (IT) network and/or a business (cooperate) network. Generally, an IT network or business network may want to receive data from a data management and operations system (220) and/or the gas leak detection and resolution system (200) and integrate that received data with data from other information systems (e.g., business plans, shareholder meetings, economic reports, etc.). As such, an external network (e.g., PDN (280)) man include a database server (287) to store data artifacts. Further, an external network may provide dashboards (282), notifications enabled by a notifications center (284), and analytics (288) capabilities using received data to one or more business users. Additionally, an external network (e.g., PDN (280)) may provide a convenient interface for the integration of additional third-party software and features (e.g., 3$^{rd}$ party integrations (286)).

While it may be useful for an external network (e.g., PDN (280)) to receive data from a data management and operations system (220) and/or the gas leak detection and resolution system (200), it is generally considered a bad practice for the data management and operations system (220) and/or the gas leak detection and resolution system (200) to receive data and/or commands from an external network. This is because a compromise (e.g., security breach) in the external network would allow an adverse party to potentially control, alter, and negatively affect a gas-handling system that could result in injury to both the gas-handling system and human operators. As a security measure, data exchanged from a data management and operations system (220) and/or the gas leak detection and resolution system (200) to an external network is passed through a security layer (270). In accordance with one or more embodiments, the security layer (270) consists of multiple firewalls, for example, a facility firewall and a corporate firewall with a demilitarized zone (DMZ) network in the middle. In some embodiments, the security layer (270) further includes a data diode installation to prevent data traffic from an external network to the data management and operations system (220) and/or the gas leak detection and resolution system (200).

Figure 3:
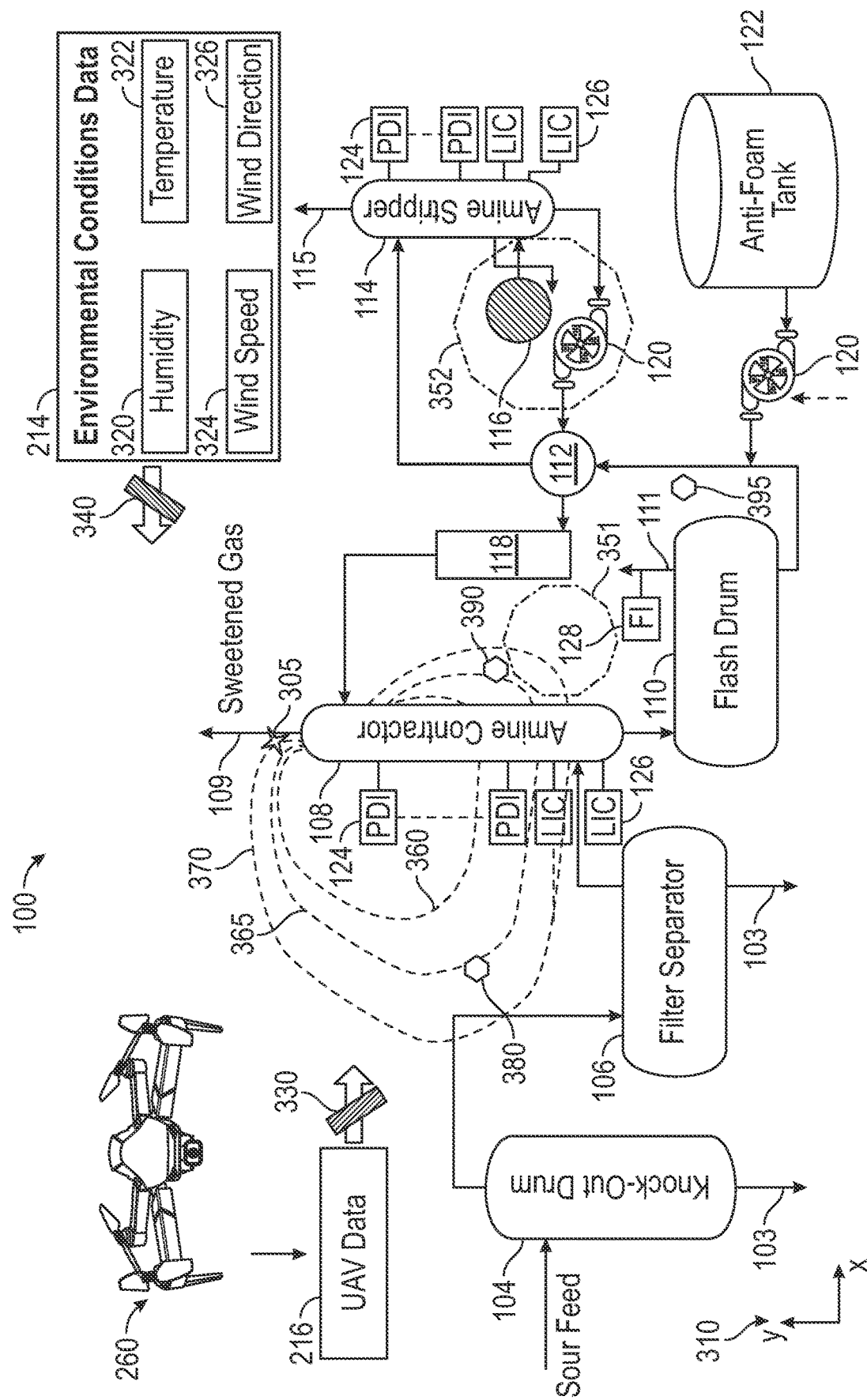
FIG. 3 depicts an example gas processing plant and aspects of a gas leak detection and resolution system, in accordance with one or more embodiments.

Turning to FIG. 3, FIG. 3 depicts the example gas processing plant (100) of FIG. 1 but some features have been removed to prevent cluttering of the figure and to promote clarity. FIG. 3 depicts various components of the gas leak detection and resolution system (300) and associated sensors (e.g., gas leak sensors, environmental sensors) in relation to the example gas processing plant (100). Further, FIG. 3 depicts an example usage of the gas leak detection and resolution system (200) during an active gas leak. It is emphasized that FIG. 3, and its accompanying description herein, are provided as an example to aid in understanding. Further, the example depicted by FIG. 3 should not impose a limitation on the instant disclosure.

As seen in FIG. 3, a first gas leak sensor (380), a second gas leak sensor (390), and third gas leak sensor (395) are located at various locations in the gas processing plant (100). The first gas leak sensor (380), second gas leak sensor (390), and third gas leak sensor (395) may be indexed with the numbers 1, 2, and 3, respectively. As such, in the example provided in FIG. 3, the position of the first gas leak sensor (380), second gas leak sensor (390), and third gas leak sensor (395) may be given relative to a coordinate system (310) as $(x_1, y_1)$, $(x_2, y_2)$, and $(x_3, y_3)$, respectively. These coordinates may be represented using a gas leak sensor position vector known by, or stored in, the gas leak detection and resolution system (200).

In FIG. 3, a gas leak (e.g., gas leak A (305)) is located on a pipeline transporting decontaminated (or "sweetened") gas (109). At an instance in time, the leaked gas is enclosed by an area represented by the current boundary (365). The leaked gas contacts the first gas leak sensor (380) and the second gas leak sensor (390) such that these sensors send an alert of a detected gas to the gas leak detection and resolution system (200) as gas leak sensory data (216). Given the positions of the gas leak sensors in contact with the leaked gas, the gas leak detection and system (200) dispatches a UAV (260) to a prescribed destination near the first and second gas leak sensors. For example, in one or more embodiments, the prescribed destination is determined by the gas leak detection and resolution system (200) as the spatial average of the coordinates of the gas leak sensors in contact with the leaked gas, where the spatial average is conducted over each axis of the coordinate system (310), independently. That is, in the example shown in FIG. 3, the destination of the UAV (260) is given as $((x_1+x_2)/2, (y_1+y_2)/2)$. In general, a UAV (260) may be dispatched to the location $$\left( \frac{\sum_{i \in \{cgls\}} x_i}{\sum_{i \in \{cgls\}} 1}, \frac{\sum_{i \in \{cgls\}} y_i}{\sum_{i \in \{cgls\}} 1} \right),$$

where the set "cgls" contains the indices for each gas leak sensor in contact with the leaked gas, or "contacted gas leak sensor." Further, UAV (260) may be instructed to arrive at, or circle about, the prescribed destination. In one or more embodiments, the UAV (260) may be configured, through use of its object detection and avoidance system, to maintain a user-defined distance X from all objects. Further, the UAV (260) may be configured to maintain a user-defined distance Y from ground level. In one or more embodiments, the user-defined distances X and Y are each set to 30 meters.

The UAV (260) transmits UAV data (216) (e.g., wireless data transmission A (330)) such as the location and orientation of the UAV (260), visual images, and thermal images to the gas leak detection and resolution system (200). Further, as graphically depicted in FIG. 3, environmental conditions data (214) is transmitted to the gas leak detection and resolution system (200) (e.g., data transmission B (340)). The environmental conditions data (214) may include measurements from one or more environmental sensors. The measurements may include but are not limited to humidity (320), ambient temperature (322), wind speed (324), wind direction (326), and barometric pressure. In some instances, the exact locations of the one or more environmental sensors is known by—or may be transmitted to—the gas leak detection and resolution system (200).

In one or more embodiments, the gas leak detection and resolution system (200) constructs an incident model (212). The incident model (212) may provide a visualization of the gas leak (e.g., gas leak A (305)) and its location within the gas-handling system (e.g., gas processing plant (100)), where the incident model (212) may provide a 2D or 3D rendering of the gas-handling system. For example, the incident model (212) may display a diagram like that of FIG. 3 indicating the location of the gas leak (gas leak A (305)) and the boundary of a gas cloud (from the leaked) gas as a function in time (e.g., current boundary (365)). The incident model (212) may integrate features of the UAV data (216), gas leak locator (204), gas leak spread predictor (206), risk and impact analysis module (208), and the mitigation recommendation module (210). In one or more embodiments, the incident model (212) provides an interactive interface displaying the spread of the gas leak at various instances in time (using the gas leak spread predictor (206)). For example, FIG. 3 depicts the spread of the leaked gas at a future instance in time (e.g., forward boundary prediction (370)).

In one or more embodiments, the gas leak spread predictor (206) and structure model of the gas-handling system (e.g., gas processing plant (100)) are used to identify high-risk areas; where such determinations may be performed by the risk and impact analysis module (208). A high-risk area may include a region or volume where a leaked gas may accumulate in higher concentrations and/or near an ignition source. FIG. 3 depicts two identified high-risk areas that present an explosion risk, namely, explosion risk area A (351) and explosion risk area B (352). In one or more embodiments, high-risk areas may be displayed graphically using the incident model (212).

FIG. 3 further depicts the spread of the leaked gas at a previous instance in time (e.g., backward boundary prediction (360)), for example, before the leaked gas contacted a gas leak sensor. In one or more embodiments, prediction of prior gas leak spread may be used by the gas leak locator (204) to localize the gas leak with reduced uncertainty.

Figure 4:
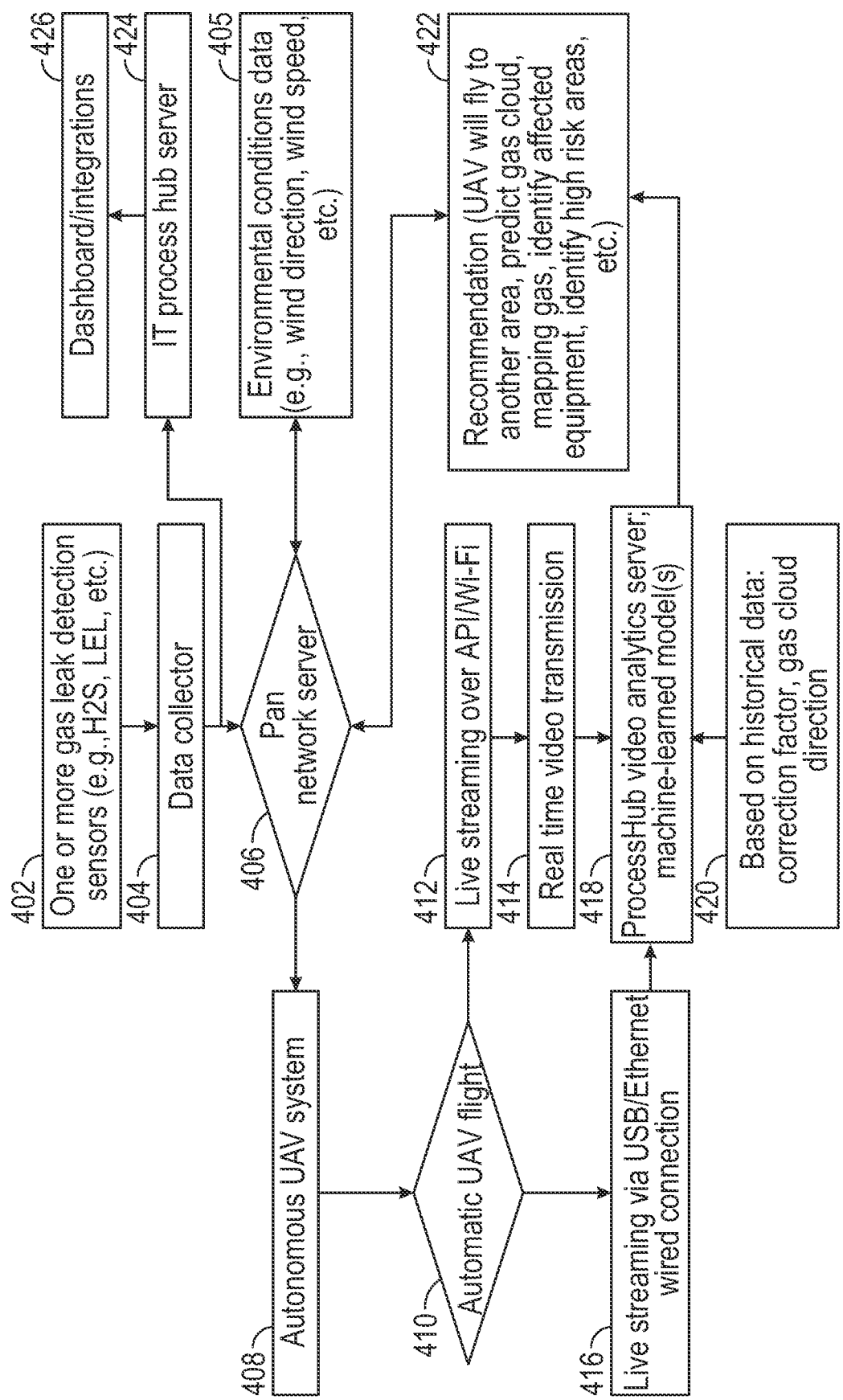
FIG. 4 depicts a system in accordance with one or more embodiments.

FIG. 4 depicts a flowchart outlining the flow of data and one or more processes that may be undertaken by the gas leak detection and resolution system (200) in accordance with one or more embodiments. As seen in FIG. 4, in Block 402 one or more gas leak sensors are disposed near or throughout a gas-handling system. The one or more gas leak detection sensor may include a H2S sensor and/or a LEL sensor. Measurements recorded by the one or more gas leak detection sensor may be collected by a data collector as seen in Block 404. The data collector may consist of one or more receivers configured to receive and parse transmitted data from the one or more gas leak detection sensors. The data collector may be used to preprocess received data and record values to a database or other memory system. In Block 405, environmental conditions data such as wind speed and wind direction are measured and received. In Block 406, data is transferred to various components and/or modules of the system using a personal area network (PAN) server, for example, a server of the data management and operations system (220) (e.g., a PI server).

In Block 408, received gas leak detection sensor data and environmental conditions data, is received by an autonomous UAV system. In Block 410, dependent on the autonomous UAV system, a UAV may be dispatched and the UAV may be navigated through an automatic UAV flight control system. Data acquired by the UAV (e.g., visual images) may be transmitted wirelessly using Wi-Fi as depicted in Block 412, where the acquired images may be received as a video feed in real time allowing for real time video transmission as depicted in Block 414. In some embodiments, a wired connection such as USB and/or ethernet may be used to transfer data acquired by the UAV as depicted in Block 416 (e.g., using a ground control system). In Block 418, the video feed is processed using a processing hub (ProcessHub) (e.g., gas leak detection and resolution system (200)). The ProcessHub may include one or more servers for computational and analytics purposes as well as one or more trained machine-learned models for data processing and prediction. The ProcessHub may be informed by or make use of historical data as depicted in Block 420 (e.g., historical database (290)). In Block 422, one or more recommendations are produced (e.g., mitigation recommendation module (210)). Recommendations may include but are not limited to: specifying a new destination for the UAV; mapping and predicting the gas cloud to identify high-risk areas and affected equipment and/or processes. Recommendations, video data, sensor data, and environmental conditions data, etc., or any subset, may be sent to an external server such as an information technology (IT) processing hub (ProcessHub) server (e.g., PDN (280)) as depicted in Block 424. In Block 426, additional dashboards and third-party integrations are provided through IT ProcessHub server.

As stated, in one or more embodiments, the gas leak detection and resolution system (200) uses one or more machine-learned models. Machine learning, broadly defined, is the extraction of patterns and insights from data. The phrases "artificial intelligence", "machine learning", "deep learning", and "pattern recognition" are often convoluted, interchanged, and used synonymously throughout the literature. This ambiguity arises because the field of "extracting patterns and insights from data" was developed simultaneously and disjointedly among a number of classical arts like mathematics, statistics, and computer science. For consistency, the term machine learning, or machine-learned, will be adopted herein, however, one skilled in the art will recognize that the concepts and methods detailed hereafter are not limited by this choice of nomenclature.

Machine-learned model types may include, but are not limited to, neural networks, random forests, generalized linear models, and Bayesian regression. Machine-learned model types are usually associated with additional "hyperparameters" which further describe the model. For example, hyperparameters providing further detail about a neural network may include, but are not limited to, the number of layers in the neural network, choice of activation functions, inclusion of batch normalization layers, and regularization strength. The selection of hyperparameters surrounding a model is referred to as selecting the model "architecture." Generally, multiple model types and associated hyperparameters are tested and the model type and hyperparameters that yield the greatest predictive performance on a hold-out set of data is selected.

As noted, possible objectives of the machine-learned models used by the object detection and resolution system (200) may include detecting and identifying objects in visual images, predicting the spread of a leaked gas, determining the location of a gas leak, and identifying high-risk areas. Machine-learned models may act in coordination or independently. In one or more embodiments the results of multiple machine-learned models are used in an ensemble to form a prediction for a target quantity. In accordance with one or more embodiments, one or more machine-learned model types and associated architectures are selected and trained to perform specific tasks such as object detection and gas leak location prediction.

Figure 5:
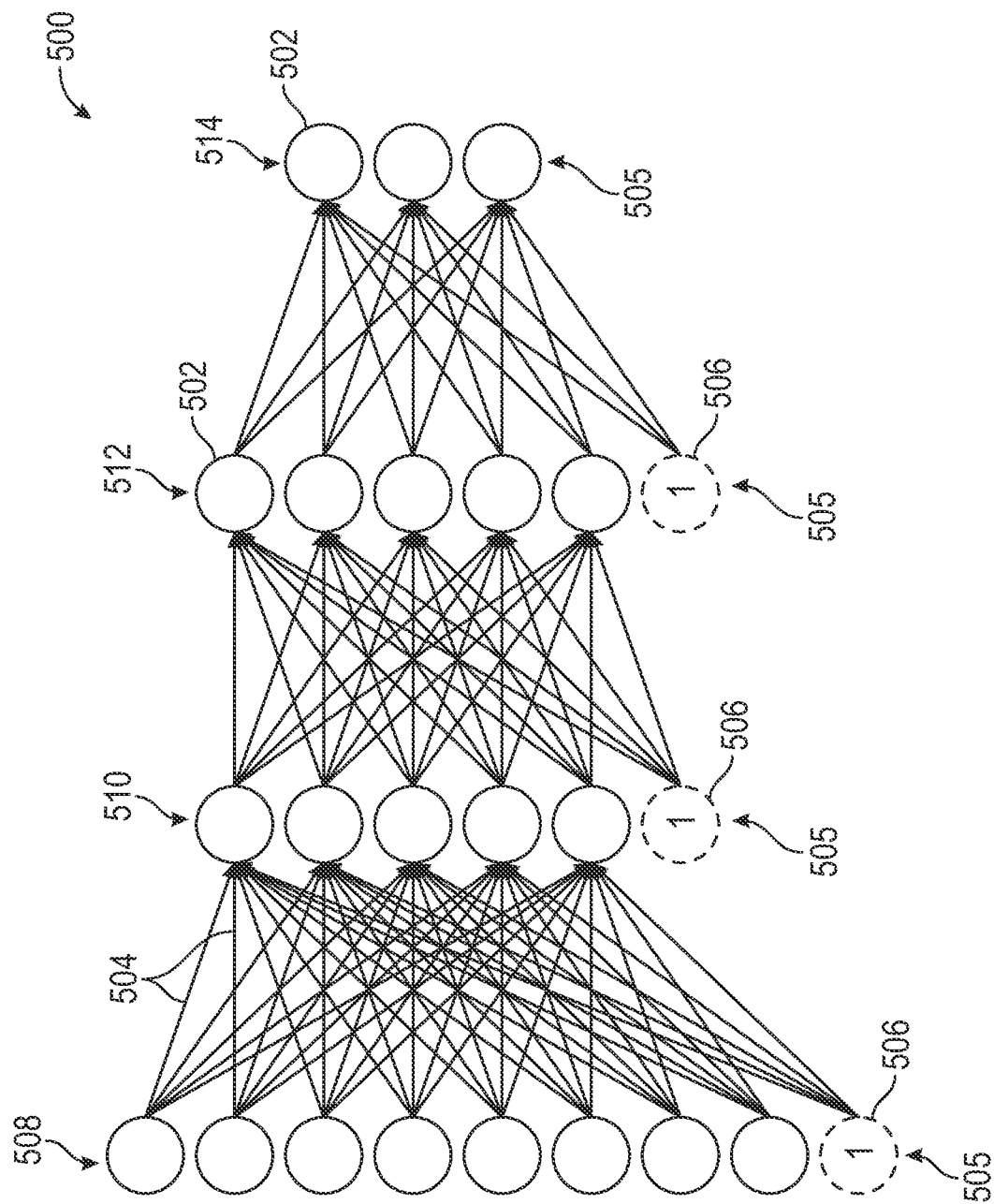
FIG. 5 depicts a neural network in accordance with one or more embodiments.

As an example of a machine-learned model that may be included in the gas leak detection and resolution system (200), FIG. 5 depicts a diagram of a neural network (500). At a high level, a neural network (500) may be graphically depicted as being composed of nodes (502), where here any circle represents a node, and edges (504), shown here as directed lines. The nodes (502) may be grouped to form layers (505). FIG. 5 displays four layers (508, 510, 512, 514) of nodes (502) where the nodes (502) are grouped into columns, however, the grouping need not be as shown in FIG. 5. The edges (504) connect the nodes (502). Edges (504) may connect, or not connect, to any node(s) (502) regardless of which layer (505) the node(s) (502) is in. That is, the nodes (502) may be sparsely and residually connected. A neural network (500) will have at least two layers (505), where the first layer (508) is considered the "input layer" and the last layer (514) is the "output layer." Any intermediate layer (510, 512) is usually described as a "hidden layer." A neural network (500) may have zero or more hidden layers (510, 512) and a neural network (500) with at least one hidden layer (510, 512) may be described as a "deep" neural network or as a "deep learning method." In general, a neural network (500) may have more than one node (502) in the output layer (514). In this case the neural network (500) may be referred to as a "multi-target" or "multi-output" network.

Nodes (502) and edges (504) carry additional associations. Namely, every edge is associated with a numerical value. The edge numerical values, or even the edges (504) themselves, are often referred to as "weights" or "parameters." While training a neural network (500), numerical values are assigned to each edge (504). Additionally, every node (502) is associated with a numerical variable and an activation function. Activation functions are not limited to any functional class, but traditionally follow the form $$A = f\left(\sum_{i \in (incoming)} [(\text{node value})_i \, (\text{edge value})_i]\right),$$

where i is an index that spans the set of "incoming" nodes (502) and edges (504) and $f$ is a user-defined function. Incoming nodes (502) are those that, when viewed as a graph (as in FIG. 5), have directed arrows that point to the node (502) where the numerical value is being computed. Some functions for $f$ may include the linear function $f(x)=x$, sigmoid function $$f(x) = \frac{1}{1 + e^{-x}},$$

and rectified linear unit function $f(x)=\max(0, x)$, however, many additional functions are commonly employed. Every node (502) in a neural network (500) may have a different associated activation function. Often, as a shorthand, activation functions are described by the function $f$ by which it is composed. That is, an activation function composed of a linear function $f$ may simply be referred to as a linear activation function without undue ambiguity.

When the neural network (500) receives an input, the input is propagated through the network according to the activation functions and incoming node (502) values and edge (504) values to compute a value for each node (502). That is, the numerical value for each node (502) may change for each received input. Occasionally, nodes (502) are assigned fixed numerical values, such as the value of 1, that are not affected by the input or altered according to edge (504) values and activation functions. Fixed nodes (502) are often referred to as "biases" or "bias nodes" (506), displayed in FIG. 5 with a dashed circle.

In some implementations, the neural network (500) may contain specialized layers (505), such as a normalization layer, or additional connection procedures, like concatenation. One skilled in the art will appreciate that these alterations do not exceed the scope of this disclosure.

As noted, the training procedure for the neural network (500) comprises assigning values to the edges (504). To begin training the edges (504) are assigned initial values. These values may be assigned randomly, assigned according to a prescribed distribution, assigned manually, or by some other assignment mechanism. Once edge (504) values have been initialized, the neural network (500) may act as a function, such that it may receive inputs and produce an output. As such, at least one input is propagated through the neural network (500) to produce an output. Recall, that a given data set will be composed of inputs and associated target(s), where the target(s) represent the "ground truth," or the otherwise desired output. The neural network (500) output is compared to the associated input data target(s). The comparison of the neural network (500) output to the target(s) is typically performed by a so-called "loss function;" although other names for this comparison function such as "error function," "misfit function," and "cost function" are commonly employed. Many types of loss functions are available, such as the mean-squared-error function, however, the general characteristic of a loss function is that the loss function provides a numerical evaluation of the similarity between the neural network (500) output and the associated target(s). The loss function may also be constructed to impose additional constraints on the values assumed by the edges (504), for example, by adding a penalty term, which may be physics-based, or a regularization term. Generally, the goal of a training procedure is to alter the edge (504) values to promote similarity between the neural network (500) output and associated target(s) over the data set. Thus, the loss function is used to guide changes made to the edge (504) values, typically through a process called "backpropagation."

While a full review of the backpropagation process exceeds the scope of this disclosure, a brief summary is provided. Backpropagation consists of computing the gradient of the loss function over the edge (504) values. The gradient indicates the direction of change in the edge (504) values that results in the greatest change to the loss function. Because the gradient is local to the current edge (504) values, the edge (504) values are typically updated by a "step" in the direction indicated by the gradient. The step size is often referred to as the "learning rate" and need not remain fixed during the training process. Additionally, the step size and direction may be informed by previously seen edge (504) values or previously computed gradients. Such methods for determining the step direction are usually referred to as "momentum" based methods.

Once the edge (504) values have been updated, or altered from their initial values, through a backpropagation step, the neural network (500) will likely produce different outputs. Thus, the procedure of propagating at least one input through the neural network (500), comparing the neural network (500) output with the associated target(s) with a loss function, computing the gradient of the loss function with respect to the edge (504) values, and updating the edge (504) values with a step guided by the gradient, is repeated until a termination criterion is reached. Common termination criteria are: reaching a fixed number of edge (504) updates, otherwise known as an iteration counter; a diminishing learning rate; noting no appreciable change in the loss function between iterations; reaching a specified performance metric as evaluated on the data or a separate hold-out data set. Once the termination criterion is satisfied, and the edge (504) values are no longer intended to be altered, the neural network (500) is said to be "trained."

Another type of machine-learned model that may be employed by the gas leak detection and resolution system (200) (e.g., for object detection) is a convolutional neural network (CNN). A CNN is similar to a neural network (500) in that it can technically be graphically represented by a series of edges (504) and nodes (502) grouped to form layers. However, it is more informative to view a CNN as structural groupings of weights; where here the term structural indicates that the weights within a group have a relationship. CNNs are widely applied when the data inputs also have a structural relationship, for example, a spatial relationship where one input is always considered "to the left" of another input. Images have such a structural relationship. Consequently, CNNs are particularly apt at processing images.

A structural grouping, or group, of weights is herein referred to as a "filter." The number of weights in a filter is typically much less than the number of inputs. In a CNN, the filters can be thought as "sliding" over, or convolving with, the inputs to form an intermediate output or intermediate representation of the inputs which still possesses a structural relationship. Like unto the neural network (500), the intermediate outputs are often further processed with an activation function. Many filters may be applied to the inputs to form many intermediate representations. Additional filters may be formed to operate on the intermediate representations creating more intermediate representations. This process may be repeated as prescribed by a user. There is a "final" group of intermediate representations, wherein no more filters act on these intermediate representations. Generally, the structural relationship of the final intermediate representations is ablated; a process known as "flattening." The flattened representation is usually passed to a neural network (500) to produce the final output. Note, that in this context, the neural network (500) is still considered part of the CNN. Like unto a neural network (500), a CNN is trained, after initialization of the filter weights, and the edge (504) values of the internal neural network (500), if present, with the backpropagation process in accordance with a loss function.

While a few types of machine-learned models have been briefly described, one with ordinary skill in the art will appreciate that the gas leak detection and resolution system (200) is not limited to only using the listed machine-learned models. Machine-learned models such as a random forest, visual transformers (ViTs), or non-parametric methods such as K-nearest neighbors or a Gaussian process may be readily inserted into this framework and do not depart from the scope of this disclosure.

Figure 6:
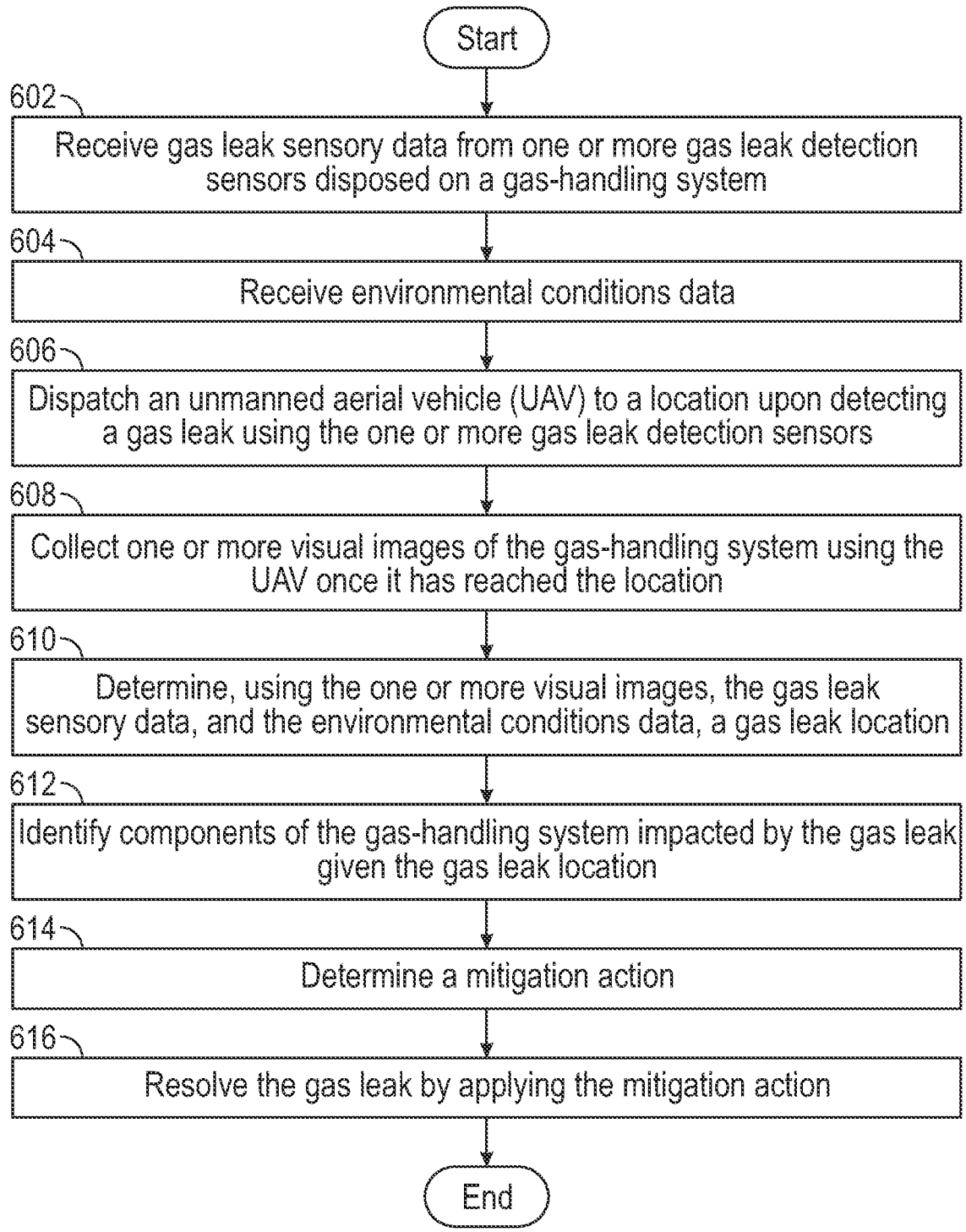
FIG. 6 depicts a flow chart, in accordance with one or more embodiments.

FIG. 6 depicts a flowchart outlining the use of the gas leak detection and resolution system (200), as described herein, in accordance with one or more embodiments. It is to be understood that one or more of the steps shown in the flowchart may be omitted, repeated, and/or performed in a different order than the order shown. Accordingly, the scope disclosed herein should not be considered limited to the specific arrangement of steps shown in the flowchart.

In Block 602, gas leak sensory data is received from one or more gas leak detection sensors disposed throughout a gas-handling system. For example, the gas leak detection sensor may be H2S sensors and LEL sensors and the gas-handling system may be a gas processing plant (100) such as that depicted in FIG. 1. The gas leak sensory data may include measured gas levels and/or a signal indicating the detection of a gas. In Block 604, environmental conditions data is received. Environmental conditions data may be received from one or more environmental sensors that measure quantities such as wind speed, wind direction, humidity, temperature, and barometric pressure. The environmental conditions data is said to pertain to the gas-handling system. That is, the environmental conditions data represents the state of the environment (or what in some instances may be referred to as local weather) surrounding the gas-handling system.

In Block 606, upon detecting a gas leak (i.e., an indication of a gas leak is present in the gas leak sensory data), an unmanned aerial vehicle (UAV) is automatically dispatched to a location. The location is determined by the gas leak detection and resolution system (200) and is intended to be in a region near the detected gas leak given, at least, the gas leak sensory data. The UAV may be flown without human interaction and/or control. That is, in one or more embodiments, the UAV is self-guided given a desired destination (the location) as determined by the gas leak detection and resolution system (200). In Block 608, once the UAV has reached the location, the UAV is used to collect one more visual images of the gas-handling system. In one or more embodiments, the UAV is further configured to collect one or more thermal images of the gas-handling system. Images, visual or thermal, may be sequenced according to time to form a video. In one or more embodiments, a video feed or transmission of the gas-handling system is provided to the gas leak detection and resolution system (200) from the UAV in real time.

In Block 610, a gas leak location indicating a more refined location estimate for the gas leak (i.e., refined beyond the location any gas leak sensors in contact with the leaked gas) is determined using the gas leak sensory data, environmental conditions data, and the one or more visual images. In one or more embodiments, a boundary of a gas cloud formed by the gas leak is also determined. In one or more embodiments, the gas leak location is determined by propagating the boundary of the gas cloud backwards in time. In Block 612, components and/or processes affected by the gas leak are identified given the gas leak location. In one or more embodiments, the gas leak detection and resolution system (200) further constructs an incident model that includes a graphical depiction of the gas-handling system and the gas leak location. In one or more embodiments, the gas leak detection and resolution system (200) further identifies regions (e.g., areas or volumes) with an explosive risk. For example, regions that have, or will have (based on a predicted future gas cloud boundary), high concentrations of gas or a combustible gas and/or gas-air mixture. Regions with an explosive risk may also include an ignition source determined using the one or more thermal images. In some embodiments, the incident model may further depict the boundary of the gas cloud of the leaked gas at various instances in time as well as potential ignitions sources and regions with an explosive risk.

In Block 614, a mitigation action is determined. In one or more embodiments, more than one mitigation action or procedure may be recommended to a user. Mitigation actions may include but are not limited to: shutting down equipment and/or processes affected by the gas leak; altering process parameters of the gas-handling system to protect equipment and optimize production given the presence of the gas leak; evacuate human operators and personnel from high risk areas (e.g., regions with an explosive risk); and shutting down equipment and/or processing acting as a potential ignition source. In Block 616, the mitigation action or recommendation provided by the gas leak detection and resolution system (200) is applied to the gas-handling system to resolve the gas leak and restore the operation of the gas-handling system. In one or more embodiments, a mitigation action is automatically selected and applied by the gas leak detection and resolution system (200), for example, by transmitting a control signal to the gas-handling system (or a control system of the gas-handling system).

Embodiments of the present disclosure may provide at least one of the following advantages. The gas leak detection and resolution system (200) described herein may be used with any facility handling hydrocarbons (downstream or upstream) that may face upset conditions due to a gas leak. The gas leak detection and resolution system (200) allows for quick isolation as well as consideration of how to minimize the impact on the facility throughput and operation. The gas leak detection and resolution system (200) can be applied to any gas-handling system (i.e., not just systems related to hydrocarbons). The gas leak detection and resolution system (200) described herein integrates multiple process systems using field data, process configuration, and logic algorithms (e.g., machine-learned models) to provide an immediate graphical solution for containing a gas leak while minimizing production impact without the potential pitfalls of human error.

FIG. 7 depicts a block diagram of a computer system (700) used to provide computational functionalities associated with the methods, functions, processes, flows, and procedures as described in this disclosure, according to one or more embodiments. One or more computers, such as that depicted in FIG. 7, may be used by, interfaced with, or included in the gas leak detection and resolution system (200) described herein. The illustrated computer (702) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702) and responding to the received requests by processing the said requests in an appropriate software application). In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713)). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or another suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704) includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). The memory may be a non-transitory computer readable medium. For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), wherein each computer (702) communicates over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. Although multiple dependent claims are not introduced, it would be apparent to one of ordinary skill that the subject matter of the dependent claims of one or more embodiments may be combined with other dependent claims.

What is claimed is:

1. A method, comprising:
    receiving gas leak sensory data from one or more gas leak detection sensors disposed on a gas-handling system, wherein a sensor location of each of the one or more gas leak detection sensors is known or comprised by the gas leak sensory data;
    receiving environmental conditions data;
    detecting, with at least one sensor of the one or more gas leak detection sensors, a gas leak;
    dispatching an unmanned aerial vehicle (UAV) to a location upon detecting the gas leak using the at least one gas leak detection sensor, wherein the location is based on the sensor location of the at least one gas leak detection sensor;
    collecting one or more visual images and one or more thermal images of the gas-handling system using the UAV once the UAV has reached the location, wherein the one or more thermal images correspond to a temperature of one or more objects of the gas-handling system;
    determining, using the one or more visual images, the gas leak sensory data, and the environmental conditions data, a refined gas leak location, wherein the refined gas leak location localizes the gas leak beyond the location of the at least one sensor;
    identifying components of the gas-handling system impacted by the gas leak given the gas leak location;
    determining a mitigation action; and
    resolving the gas leak by applying the mitigation action.

2. The method of claim 1, further comprising determining a boundary of a gas cloud formed by the gas leak.

3. The method of claim 2, wherein the gas leak location is determined by propagating the boundary of the gas cloud backwards in time.

4. The method of claim 2, wherein the boundary of the gas cloud is determined using a computational fluids model parameterized by the environmental conditions data.

5. The method of claim 2, wherein the boundary of the gas cloud formed by the gas leak accounts for equipment and physical structures of the gas-handling system.

6. The method of claim 1, further comprising constructing an incident model, wherein the incident model graphically depicts the gas-handling system, the gas leak location, and components of the gas-handling system impacted by the gas leak.

7. The method of claim 1, wherein the mitigation action comprises shutting down all components of the gas-handling system identified as impacted and repairing the gas leak.

8. The method of claim 1, wherein the UAV is dispatched to the location automatically and flown without human interaction.

9. The method of claim 1, further comprising transmitting a command signal to the gas-handling system to shut down all components of the gas-handling system identified as impacted by the gas leak.

10. The method of claim 1, further comprising:
    determining, with the one or more thermal images, a first ignition source; and determining a first region with an explosive risk based on the first ignition source and the refined gas leak location, wherein the first region comprises the first ignition source.

11. A system, comprising:
one or more gas leak detection sensors disposed throughout a gas-handling system, wherein a sensor location of each of the one or more gas leak detection sensors is known or comprised by gas leak sensory data;
an autonomous unmanned aerial vehicle (UAV) system configured to dispatch a UAV to a desired location, wherein the UAV is flown without human interaction and is configured to acquire one or more visual images and one or more thermal images upon arriving at the desired location, wherein the one or more thermal images correspond to a temperature of one or more objects of the gas-handling system; and
a computer communicably connected to the autonomous UAV system, comprising:
one or more computer processors, and
a non-transitory computer readable medium storing instructions executable by a computer processor, the instructions comprising functionality for:
receiving the gas leak sensory data from the one or more gas leak detection sensors;
detecting, based on the gas leak sensory data, a gas leak with at least one sensor of the one or more gas leak detection sensors;
determining the desired location based on the sensor location of the at least one gas leak detection sensor;
transmitting a signal to the autonomous UAV system to dispatch the UAV to the desired location upon detecting the gas leak;
receiving environmental conditions data;
receiving the one or more visual images and the one or more thermal images;
determining, using the one or more visual images, the gas leak sensory data, and the environmental conditions data, a refined gas leak location, wherein the refined gas leak location localizes the gas leak beyond the location of the at least one sensor;
identifying components of the gas-handling system impacted by the gas leak given the gas leak location; and
determining a mitigation action.

12. The system of claim 11, wherein the instructions further comprise functionality for determining a boundary of a gas cloud formed by the gas leak.

13. The system of claim 11, wherein the instructions further comprise functionality for constructing an incident model, wherein the incident model graphically depicts the gas-handling system, the gas leak location, and components of the gas-handling system impacted by the gas leak.

14. The system of claim 11, wherein the mitigation action comprises shutting down all components of the gas-handling system identified as impacted and repairing the gas leak.

15. The system of claim 11, wherein the instructions further comprise functionality for transmitting a command signal to the gas-handling system to shut down all components of the gas-handling system identified as impacted by the gas leak.

16. The system of claim 11, wherein the instructions further comprise functionality for:
determining, with the one or more thermal images, a first ignition source; and
determining a first region with an explosive risk based on the first ignition source and the refined gas leak location, wherein the first region comprises the first ignition source.

17. The system of claim 11, wherein the boundary of the gas cloud formed by the gas leak accounts for equipment and physical structures of the gas-handling system.

18. A non-transitory computer-readable memory comprising computer-executable instructions stored thereon that, when executed on a processor, cause the processor to perform steps comprising:
receiving gas leak sensory data from one or more gas leak detection sensors disposed on a gas-handling system, wherein a sensor location of each of the one or more gas leak detection sensors is known or comprised by the gas leak sensory data;
receiving environmental conditions data;
detecting, with at least one sensor of the one or more gas leak detection sensors, a gas leak;
dispatching an unmanned aerial vehicle (UAV) to a location upon detecting the gas leak using the at least one gas leak detection sensor, wherein the location is based on the sensor location of the at least one gas leak detection sensor;
collecting one or more visual images and one or more thermal images of the gas-handling system using the UAV once the UAV has reached the location, wherein the one or more thermal images correspond to a temperature of one or more objects of the gas-handling system;
determining, using the one or more visual images, the gas leak sensory data, and the environmental conditions data, a refined gas leak location, wherein the refined gas leak location localizes the gas leak beyond the location of the at least one sensor;
identifying components of the gas-handling system impacted by the gas leak given the gas leak location; and
determining a mitigation action.

19. The non-transitory computer-readable memory of claim 18, wherein the instructions further comprise functionality for determining a boundary of a gas cloud formed by the gas leak.

20. The non-transitory computer-readable memory of claim 18, wherein the instructions further comprise functionality for constructing an incident model, wherein the incident model graphically depicts the gas-handling system, the gas leak location, and components of the gas-handling system impacted by the gas leak.

* * * * *